US00PP25223P2

(12) United States Plant Patent
Finn

(10) Patent No.: US PP25,223 P2
(45) Date of Patent: Jan. 13, 2015

(54) STRAWBERRY PLANT NAMED 'SWEET SUNRISE'

(50) Latin Name: ***Fragaria×ananassa* Duchesne ex Rozier.**
Varietal Denomination: Sweet Sunrise

(71) Applicant: The United States of America, as represented by the Secretary of Agriculture, Washington, DC (US)

(72) Inventor: Chad E Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 10 days.

(21) Appl. No.: 13/694,950

(22) Filed: Jan. 22, 2013

(51) Int. Cl.
*A01H 5/00* (2006.01)

(52) U.S. Cl.
USPC ..... Plt./208

(58) Field of Classification Search
USPC ..... Plt./208
See application file for complete search history.

(56) References Cited

U.S. PATENT DOCUMENTS

PP8,346 P 8/1993 Nelson et al.
PP8,649 P 3/1994 Sjulin et al.
PP8,659 P 3/1994 Voth et al.
PP8,660 P 3/1994 Voth et al.
PP8,662 P 3/1994 Bringhurst et al.
PP8,663 P 3/1994 Voth et al.
PP8,708 P 5/1994 Voth et al.
PP8,745 P 5/1994 Sjulin et al.
PP8,853 P 8/1994 Buszard et al.
PP8,970 P 11/1994 Sjulin et al.
PP9,130 P 5/1995 Sjulin et al.
PP9,310 P 10/1995 Moore
PP10,191 P 1/1998 Luby et al.
PP10,402 P 5/1998 Hureau
PP10,460 P 6/1998 Khanizadeh et al.
PP10,960 P 6/1999 Lopez
PP11,277 P 3/2000 Gilford et al.
PP12,067 P2 8/2001 Moore
PP16,228 P3 1/2006 Shaw et al.
PP16,480 P3 4/2006 Weber et al.
PP16,571 P3 5/2006 Weber et al.
PP17,404 P3 2/2007 Luby et al.
PP19,472 P3 11/2008 Shaw et al.
PP22,589 P3 3/2012 Larson et al.
PP22,781 P2 6/2012 Moore

*Primary Examiner* — Anne Grunberg
(74) *Attorney, Agent, or Firm* — Gail E. Poulos; John Fado; Lesley Shaw

(57) ABSTRACT

This invention relates to new and distinct cultivar of strawberry plant named 'Sweet Sunrise'. The new cultivar is primarily characterized by its early ripening and its medium-large, conical fruit that have outstanding processing characteristics including deep red internal and external color, sweet flavor, and very easy calyx removal, as well as vigorous, productive plants that are tolerant to biotic and abiotic stress.

5 Drawing Sheets

Latin name of the genus and species of the plant claimed: 'SWEET SUNRISE' is a new strawberry plant that is *Fragaria×ananassa* Duchesne ex Rozier.

Variety denomination: The new strawberry plant claimed is of the variety denominated 'Sweet Sunrise', *Fragaria×ananassa* Duchesne ex Rozier.

BACKGROUND OF THE NEW PLANT

The present invention relates to a new and distinct strawberry cultivar strawberry designated 'Sweet Sunrise' and botanically known as *Fragaria×ananassa* Duchesne ex Rozier. This new strawberry cultivar was discovered in Corvallis, Oreg. in June 2000 and originated from a cross between the female parent 'Puget Reliance' (U.S. Plant Pat. No. 9,310) and the male parent B 754 (unpatented). The original seedling of the new cultivar was asexually propagated by rooting daughter plants from the mother plant since 2000 in Benton County, Oreg. The present invention has been found to be stable and reproduce true to type through successive asexual propagations.

DESCRIPTION OF THE PHOTOGRAPHS

The accompanying color photographs show typical specimen's of the new cultivar at various stages of development as nearly true as it is possible to make in color reproductions.

DESCRIPTION OF THE NEW CULTIVAR

Figure 1:
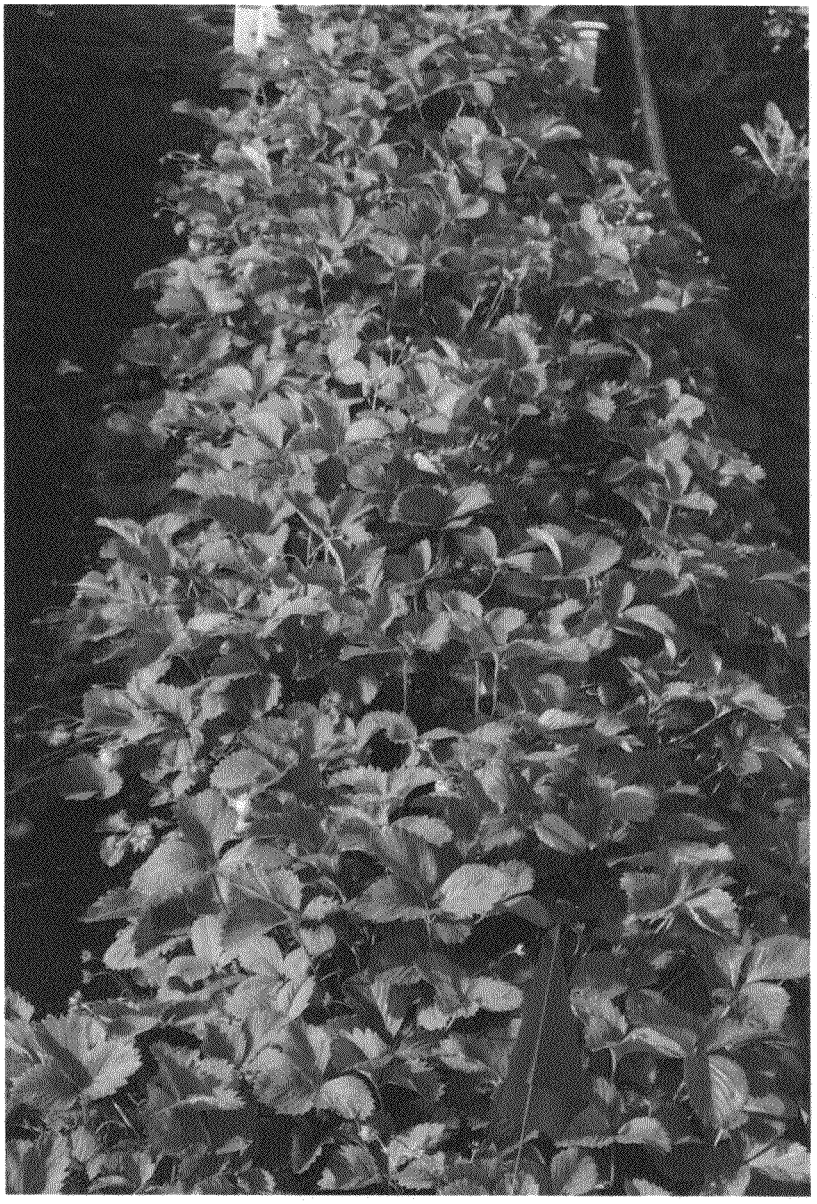
FIG. 1 shows overall plant habit.
Figure 2:
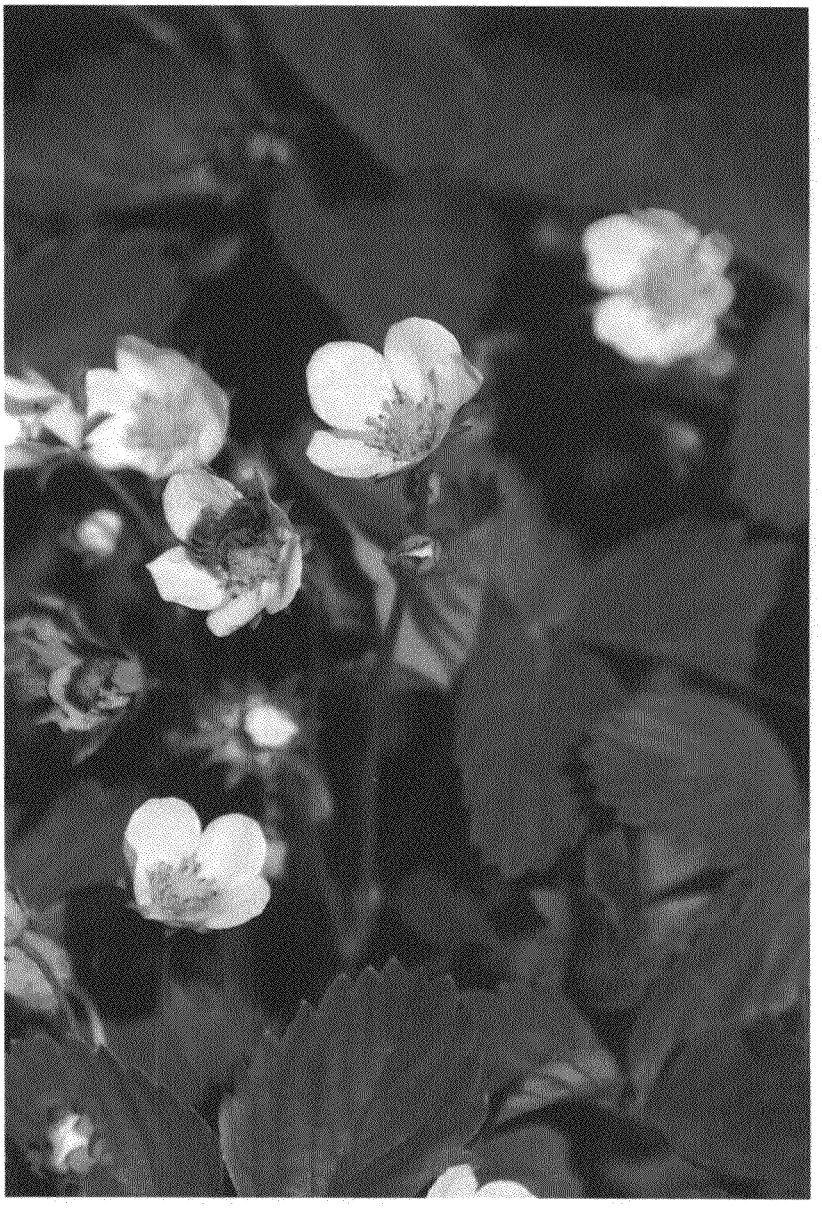
FIG. 2 shows the flower morphology.
Figure 3:
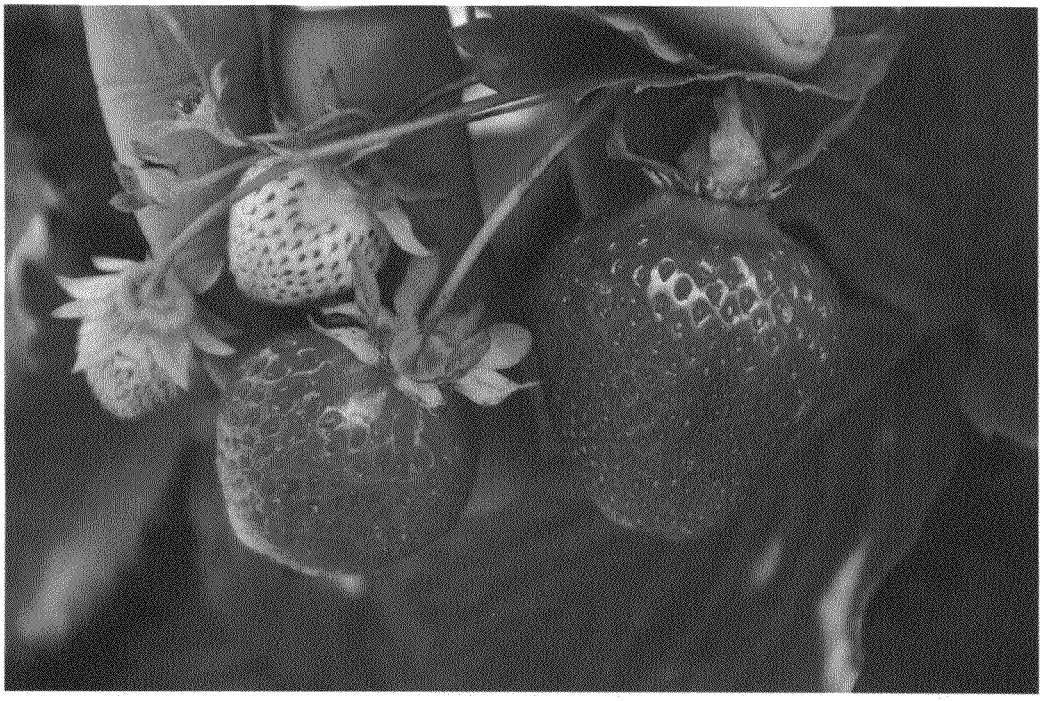
FIG. 3 shows a flower truss with fruit in a range of ripening stages.
Figure 4:
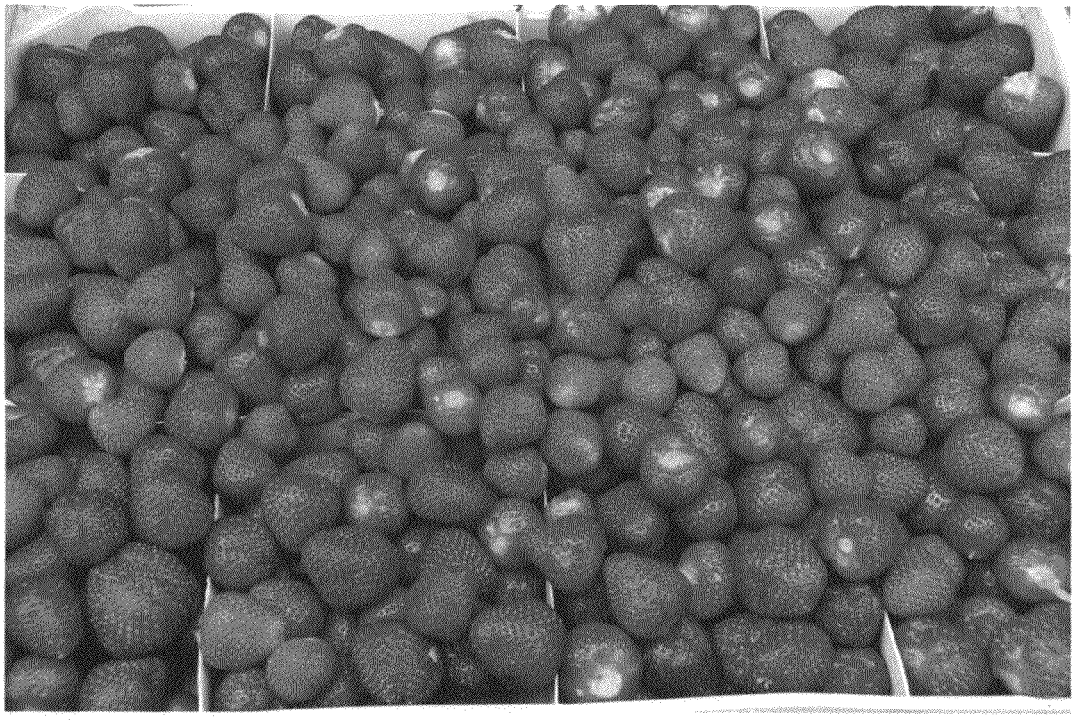
FIG. 4 shows typical fruit after harvest for processing market.
Figure 5:
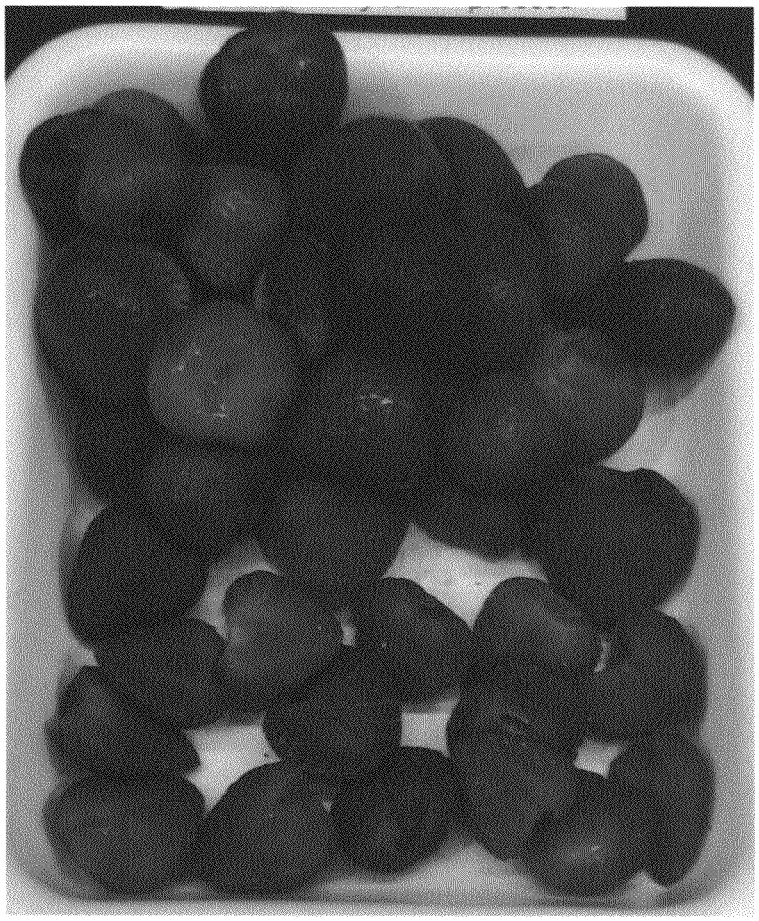
FIG. 5 shows typical entire and sliced fruit after freezing and thawing.

The following description of 'Sweet Sunrise' is based on observations taken from 2002 to 2012 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Sweet Sunrise' has not been observed under all possible environmental conditions. The botanical description of 'Sweet Sunrise' was taken from plants one year after establishment in the field. Color terminology follows The Royal Horticultural Society Colour chart. London (R.H.S.) ($5^{th}$ edition, 2007).

DETAILED BOTANICAL DESCRIPTION

Table 1 shows selected characteristics of the new cultivar compared with plant characteristics of 'Charm', (U.S. Plant patent application Ser. No. 13/694,975). Characteristics include plant height, number of crowns per plant, plant habit, bract frequency, petiole texture, petal length and width, fruit shape, and fruit weight.

TABLE 1

| Characteristic | 'Sweet Sunrise' | 'Charm' |
|---|---|---|
| Plant height (cm) | 11.9 | 20.0 |
| Number of crowns/plant | 6.2 | 11.0 |
| Habit | Upright, open globose | Upright globose |
| Bract frequency | Typically two | None |
| Texture petiole | Dense | Hirsute |
| Petal length (cm) | 1.4 | 1.0 |
| Petal width (cm) | 1.3 | 1.0 |
| Fruit shape | Conic | Conic, slight wedge |
| Weight fruit (g) | 15.4 | 14.6 |

Table 2 shows plant characteristics of the new cultivar compared with plant characteristics of 'Charm' (U.S. Plant patent application Ser. No. 13/694,975). Plant characteristics include plant height, diameter, number of crowns per plant, habit, density of individual plants and vigor.

TABLE 2

| Characteristic | 'Sweet Sunrise' | 'Charm' |
|---|---|---|
| Plant height (cm) | 11.9 | 20.0 |
| Plant diameter (cm) | 25.0 | 34.7 |
| Number of crowns/plant | 6.2 | 11.0 |
| Habit | Upright, open globose | Upright globose |
| Density of individual plant | Medium | Medium to Dense |
| Vigor | Medium | Strong |

Table 3 shows leaf characteristics of the new cultivar compared with leaf characteristics of 'Charm' (U.S. Plant patent application Ser. No. 13/694,975). Leaf characteristics include leaf type, leaf shape. leaf length, leaf width, terminal leaflet length, terminal leaflet width, terminal leaflet length to width ratio, leaf margins, shape of teeth, leaf serrations per leaflet, upper and lower leaf surface color, number of leaflets, terminal leaflet apex shape, terminal leaflet base shape, glossiness upper side leaf surface, texture upper side leaf surface, texture underside leaf surface and leaf arrangement.

TABLE 3

| Characteristic | 'Sweet Sunrise' | 'Charm' |
|---|---|---|
| Leaf type | Semi-evergreen leaves will die back to ground in severe winters | Semi-evergreen leaves will die back to ground in severe winters |
| Leaf shape | Ovate | Ovate |
| Leaf length (cm) | 7.94 | 6.98 |

TABLE 3-continued

| Characteristic | 'Sweet Sunrise' | 'Charm' |
|---|---|---|
| Leaf width (cm) | 6.76 | 6.53 |
| Terminal leaflet length (cm) | 7.72 | 7.87 |
| Terminal leaflet width (cm) | 6.27 | 6.93 |
| Terminal leaflet length/width ratio | 1.2 | 1.1 |
| Leaf margins | Single serration, coarsely serrate | Serrate |
| Shape of teeth | Pointed | Rounded |
| Leaf serrations per leaflet | 21.7 | 20.3 |
| Color mature leaves upper surface | Green Group N 137A | Green Group N 137B |
| Color mature leaves lower surface | Green Group 138C | Green Group N138C |
| Number of leaflets | 3 | 3 |
| Terminal leaflet apex shape | Obtuse | Obtuse |
| Terminal leaflet base shape | Cuneate | Cuneate |
| Glossiness upper side leaf surface | Semi-gloss | Semi-gloss |
| Texture upper side leaf surface | Very lightly tomentose | Very lightly tomentose |
| Texture underside leaf surface | Tomentulose | Tomentulose |
| Leaf arrangement | Compound with three leaflets | Compound with three leaflets |

Table 4 shows information about the petiole, the petiolule, the bract and the stipule of the new cultivar compared to 'Charm' (U.S. Plant patent application Ser. No. 13/694,975). This includes petiole length, petiole diameter, petiole pubescence, petiole color, petiolule color, petiolule length, bract frequency, texture petiole, stipule length, and stipule width.

TABLE 4

| Characteristic | 'Sweet Sunrise' | 'Charm' |
|---|---|---|
| Leaf petiole length (cm) | 10.8 | 18.0 |
| Petiole diameter (cm) | 0.27 | 0.26 |
| Petiole pubescence | Dense | Hirsute |
| Petiole color | 144C | 144C |
| Petiolule color | 144C | 144C |
| Petiolule length (cm) | 1.17 | 1.11 |
| Bract frequency | Typically two | None |
| Texture petiole | Dense | Hirsute |
| Stipule length (cm) | 2.51 | 1.96 |
| Stipule width (cm) | 1.24 | 1.01 |

Table 5 shows stolon characteristics of the new cultivar compared to 'Charm' (U.S. Plant patent application Ser. No. 13/694,975). These characteristics include the number of stolons, the anthocyanin coloration of the stolons, the thickness of the stolons, and the pubescence of the stolons.

TABLE 5

| Characteristic | 'Sweet Sunrise' | 'Charm' |
|---|---|---|
| Stolon number | 6.0 | 13.5 |
| Stolon anthocyanin | Between weak and medium | Weak |
| Stolon thickness | 0.25 | 0.26 |
| Stolon pubescence | Sparse | Sparse to medium |

Table 6 shows inflorescence characteristics of the new cultivar compared to 'Charm' (U.S. Plant patent application Ser. No. 13/694,975). These characteristics include inflorescence position relative to foliage, flower type, flower size, petal shape, relative petal spacing, petal apex shape, petal margin, petal base shape, petal length, petal width, petal length/width ratio, number of petals, petal color, stigma color, style color, anther color, filament color, and flower truss type.

TABLE 6

| Characteristic | 'Sweet Sunrise' | 'Charm' |
|---|---|---|
| Inflorescence position | Between level with and above | Between level with and above |
| Flower type | Complete simple | Complete simple |
| Flower diameter (cm) | 2.7 | 2.7 |
| Petal shape | Orbicular | Orbicular |
| Petal spacing | Overlapping | Overlapping |
| Petal apex shape | Rounded | Rounded |
| Petal margin | Entire | Entire |
| Petal base shape | Rounded | Rounded |
| Petal length (cm) | 1.43 | 1.00 |
| Petal width (cm) | 1.31 | 1.00 |
| Petal length/width ratio | 1.1 | 1.0 |
| Petal count | 5.4 | 5.1 |
| Petal color | White Group NN 155B | White Group NN155C |
| Stigma color | Yellow Group 13A | Green-Yellow Group 1B |
| Style color | Yellow Group 13A | Green-Yellow Group 1B |
| Anther color | Yellow-Orange Group 14A | Yellow-Orange Group 14A |
| Filament color | Yellow-Orange Group 14A | Yellow-Orange Group 14D |
| Blooming habit | Cyme | Cyme |

Table 7 shows fruit characteristics of the new cultivar compared to 'Charm' (U.S. Plant patent application Ser. No. 13/694,975). These characteristics include number of berries per truss, fruiting truss attitude, fruit length, fruit diameter, fruit length/width ratio, fruit weight, relative fruit size, predominant fruit shape, difference in shape between primary and secondary fruit, band without achenes, evenness of fruit surface, top color, non-blush side color, blush side color, internal color, achene color, achene count per fruit, insertion of calyx, pose of calyx segments, size of calyx in relation to fruit, ease of calyx removal, firmness of flesh, evenness of flesh color, distribution of flesh color, sweetness, acidity, Brix, pH, titratable acidity, texture when tasted, time of flowering, harvest maturity (50% of plants with ripe fruit), type of bearing, and yield.

TABLE 7

| Characteristic | 'Sweet Sunrise' | 'Charm' |
|---|---|---|
| Number of berries per fruiting truss | 5.2 | 6.8 |
| Fruiting truss attitude | Between erect and semi-erect | Between prostrate and semi-erect |
| Diameter fruit (cm) | 2.93 | 3.50 |
| Length fruit (cm) | 3.23 | 4.30 |

TABLE 7-continued

| Characteristic | 'Sweet Sunrise' | 'Charm' |
|---|---|---|
| Ratio fruit length/width | 1.1 | 1.2 |
| Weight fruit (g) | 15.4 | 14.6 |
| Relative fruit size | Medium-large | Medium |
| Predominant fruit shape | Conic | Conic, slight wedge |
| Difference in shape between primary and secondary fruits | Slight | Slight |
| Band without achenes | Very narrow | Absent or very narrow |
| Evenness of fruit surface | Even | Very even |
| Color of top of fruit | Red Group 53A | Red Group 53A |
| Non-blush side color | Red Group 53A | Red Group 53A |
| Blush side color | Red Group 53A | Red Group 53A |
| Internal flesh color | Red Group 47A (mostly uniform) | Red Group 47A (mostly uniform, slightly open core) |
| Achene color | Red Group 53A | Red Group 53B |
| Achene count | 278 | 216 |
| Insertion of calyx | Level | Level |
| Pose of calyx segments | Spreading to reflexed | Spreading |
| Size of calyx in relation to fruit | Smaller | Between same size and smaller |
| Ease of calyx removal | Easy | Very easy |
| Firmness of flesh | Firm | Medium |
| Evenness of flesh color | Even | Even |
| Distribution of flesh color | Throughout | Throughout |
| Sweetness | Strong | Strong |
| Acidity | Medium | Medium |
| Brix (percent soluble solids) | 8.27 | 7.65 |
| pH | 3.56 | 3.43 |
| Titratable acidity (g citric acid/100 g fruit) | 7.65 | 9.45 |
| Texture when tasted | Fine | Fine |
| Time of flowering | Begins late April early May, ends early-mid June | First bloom mid-late April, ends early-mid June |
| Harvest maturity (50% of plant with ripe fruit) | Early June | Mid-June |
| Type of bearing | Short-day/June-bearing | Short-day/June-bearing |
| Yield (kg/hectare) | 34455 | 38063 |

COMPARISON WITH PARENTAL GENOTYPES

When 'Sweet Sunrise' is compared to female parent 'Puget Reliance' (U.S. Plant Pat. No. 9,310), the fruit are deeper red, firmer, and more conically shaped and the plants less susceptible to foliar disease. When 'Sweet Sunrise' is compared to the male parent B 754 (unpatented) the fruit are deeper red, firmer and the plants better adapted to biotic and abiotic stress in the Pacific Northwest.

I claim:

1. A new and distinct cultivar of strawberry plant as described and shown herein.

* * * * *